United States Patent [19]

Toth et al.

[11] 4,456,601
[45] Jun. 26, 1984

[54] 3-CHLORO-PREGNANE DERIVATIVES AND A PROCESS FOR THE PREPARATION THEREOF

[75] Inventors: Jozsef Toth; Gyorgy Hajos; Gyorgy Fekete; Istvan Horvath; László Szporny; Anna Boor nee Mezei; Peter Aranyi; Aniko Naray; Sandor Gorog; Sandor Holly; Csaba Molnar, all of Budapest, Hungary

[73] Assignee: Richter Gedeon Vegyeszeti Gyar Rt., Budapest, Hungary

[21] Appl. No.: 434,335

[22] Filed: Oct. 14, 1982

[30] Foreign Application Priority Data

Oct. 15, 1981 [HU] Hungary ............................. 2976/81

[51] Int. Cl.³ ...................... C07J 71/00; A61K 31/56
[52] U.S. Cl. ........................... 424/241; 260/239.55 D
[58] Field of Search ............... 260/239.55 D; 424/241

[56] References Cited

U.S. PATENT DOCUMENTS 4,255,331 3/1981 MacDonald ............... 260/239.55 D

Primary Examiner—Elbert L. Roberts
Attorney, Agent, or Firm—Karl F. Ross; Herbert Dubno

[57] ABSTRACT

New $\Delta^{1,3,5}$-3-chloro-pregnane derivatives of the general formula (I),

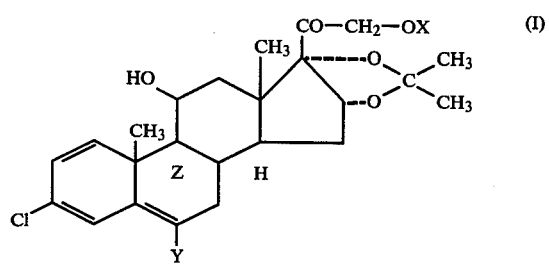

wherein
X is hydrogen atom, acetyl group or a chloroacetyl group, and
Y and Z represent hydrogen atom or a halogen atom, with the proviso that at least one of them is other than hydrogen, are prepared by reacting a $\Delta^{1,4}$-3-oxo-pregnane derivative of the general formula (II),

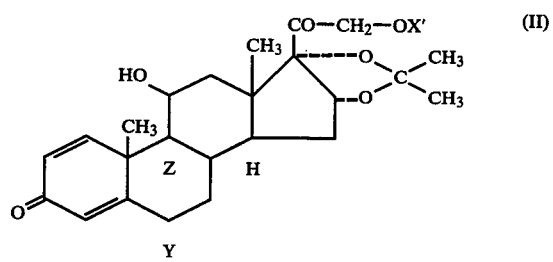

wherein X' is acetyl group or a chloroacetyl group and Y and Z are as defined above, with a chloromethyleneiminium salt of the general formula (III),

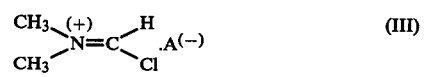

wherein $A^{(-)}$ is a salt-forming anion, in an aprotic solvent in the presence of a tertiary base, and, if desired, subjecting the resulting product to hydrolysis.

The compounds of the general formula (I) exert antiphlogistic effects and can be used in the therapy for the treatment of inflammations.

7 Claims, No Drawings

3-CHLORO-PREGNANE DERIVATIVES AND A PROCESS FOR THE PREPARATION THEREOF

The invention relates to new 3-chloro-pregnane derivatives of the formula (I),

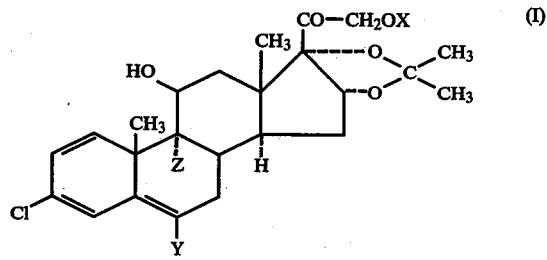

wherein
X is hydrogen, acetyl or chloroacetyl, and
Y and Z represent hydrogen or halogen, with at least one of them being other than hydrogen,
and pharmaceutical compositions containing the same, as well as to a process for the preparation thereof.

It has been found that the new compounds of the formula (I), which can be prepared by reacting the respective $\Delta^{1,4}$-3-oxo-pregnane derivatives with a chloromethyleneiminium salt, possess significant antiphlogistic effects.

Iminium salts have been used increasingly widespread in preparative organic chemistry in the last few years [see e.g. H. Böhme and H. G. Viehe: "Iminium Salts in Organic Chemistry", with particular respect to the chapter entitled "The Vilsmeier-Haack-Arnold Acylations" (Advances in Organic Chemistry: Methods and Results, Ed.: E. C. Taylor, Vol. 9, Part 1, pp. 225-333; J. Wiley and Sons, Inc., 1976)].

It appears clearly from the cited reference that chloromethyleneiminium salts of the formula (III),

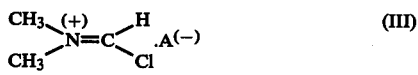

wherein $A^{(-)}$ is a salt-forming anion, such as a chloride, bromide, dichlorophosphate, sulfate or fluoroborate anion, also known as "Vilsmeier reagents", can be used variously to form new carbon-carbon bonds by introducing a formyl group onto a reactive carbon atom. This reaction has also been utilized in the field of steroid chemistry; thus e.g. the 3-enolethers of $\Delta^4$-3-oxo-pregnane derivatives can be treated with Vilsmeier reagents to obtain the respective 6-formyl compounds with good yields. The nature of anion $A^{(-)}$ in the reactant influences the course of the reaction [see Tetrahedron 25, 1155 (1969)]. Free $\Delta^4$-3-oxo-oestrane derivatives, furthermore $\Delta^4$-3-oxo-androstane, $\Delta^{4,6}$-3-oxo-oestrane and -androstane derivatives yield variously formylated 3-chloro-steroid-dienes or -trienes in this reaction [see Tetrahedron Letters 1965, 137; Chem. Ber. 101, 2393 (1968)], 5α-androstane-3-one derivatives convert into the respective 3-chloro-2,4-diformyl compounds under severe reaction conditions (J. Chem. Soc. 1965, 788), whereas for 19-nor-pregna-4,6-diene-3,20-dione derivatives the aromatization of ring A also takes place in addition to chlorination and formylation [Chem. Ber. 101, 2393 (1968)].

In our research directed to the preparation of new pregnane derivatives with favorable therapeutical properties, the reactions of $\Delta^{1,4}$-3-keto-pregnane derivatives with Vilsmeier reagents were tested as well. It is well known that $\Delta^{1,4}$-3-oxo-pregnane compounds derived from pregnane compounds with trans/anti/trans/anti/-trans anellation contain an oxo group with very low reactivity in position 3. This oxo group does not form enol ethers, enol esters, enamines or open or cyclic ketals, whereas these reactions proceed generally with good yields on compounds with saturated A ring or on $\Delta^4$-3-oxo derivatives (see e.g. J. Fried and J. A. Edwards: "Organic Reactions in Steroid Chemistry", van Nostrand Reinhold Co., 1972, p. 394).

Now it has been found, unexpectedly, that when a $\Delta^{1,4}$-3-oxo-pregnane derivative of the formula (II),

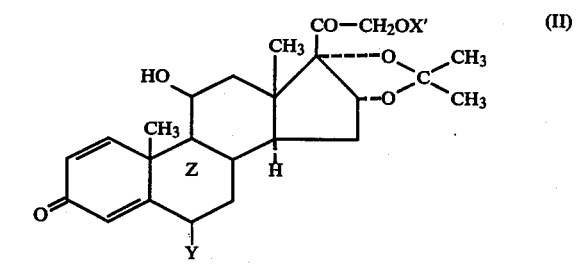

wherein X' is acetyl group or chloroacetyl group and Y and Z are as defined above, is reacted with a Vilsmeier reagent, the less reactive 3-oxo group of the pregnane derivative eliminates, a $C_3$—Cl bond forms, and a double bond system, consisting of three double bonds in rings A and B of the steroid skeleton, appears in the molecule.

It has also been found that when a compound of the formula (II) is reacted with a Vilsmeier reagent in an aprotic organic solvent in the presence of a tertiary base, no other reaction than those discussed above (exchange of the 3-oxo group for chlorine, formation of three unsaturated bonds) occurs in the molecule. This selectivity is rather surprising, since, as discussed in the literature [Tetrahedron Letters 1965, 137; Chem. Ber. 101, 2393 (1968)], 3-oxo-steroids also undergo single or multiple formylation when reacting them with Vilsmeier reagent. It is particularly surprising that the 11-hydroxy group of the compounds having the formula (II) remains unchanged, although the formylation of the 11-hydroxy group of a $\Delta^4$-3-oxo-pregnane derivative reported in Tetrahedron 25, 1155 (1969) proceeds so quickly upon contacting it with a Vilsmeier reagent that the free 11-hydroxy compound can be obtained only with a very low yield.

Based on the above, the invention relates to a process for the preparation of new $\Delta^{1,3,5}$-3-chloro-pregnane derivatives of the formula (I), wherein X, Y and Z are as defined above. According to the invention a $\Delta^{1,4}$-3-oxo-pregnane derivative of the formula (II), wherein X' is acetyl or chloroacetyl and Y and Z are as defined above, is reacted with a chloromethyleneiminium salt of the formula (III), wherein $A^{(-)}$ represents a salt-forming anion, preferably a dichlorophosphate ion ($O_2PCl_2$), in an aprotic solvent in the presence of a tertiary base, and, if desired, a resulting compound of the formula (I), wherein X is acetyl or chloroacetyl, is subjected to hydrolysis to obtain a compound of the formula (I) wherein X is hydrogen.

The steroids of the formula (II), used as starting substances in the process of the invention, can be prepared by subjecting the respective 21-hydroxy-steroids to selective acylation. These steroids with a free hydroxy group in position 21 are known compounds. The Vilsmeier reagent of the formula (III) is prepared preferably directly in the reaction medium by reacting dimethyl formamide with phosphorous oxychloride in a dry aprotic solvent. It is preferred to use halogenated lower hydrocarbons, particularly dichloromethane and/or chloroform, as aprotic solvents.

The reaction according to the invention is performed preferably as follows: The starting substance of the formula (II) is dissolved in a dry organic solvent, preferably in the same solvent as utilized in the preparation of the Vilsmeier reagent of the formula (III), a tertiary base, preferably pyridine or a homologue thereof, such as picoline, lutidine or collidine, is added to the solution, and the resulting mixture is added to the solution of the Vilsmeier reagent, prepared as discussed above, at a temperature between −10° C. and room temperature, preferably at −10° C. to 0° C. The reagent of the formula (III) is utilized preferably in excess; 3 molar equivalents of the reagent of the formula (III) can be used for one mole of the starting pregnane derivative. The reaction proceeds within a period of from 20–30 minutes to 5 hours, depending on the starting substances applied. During this period the reaction mixture is allowed to warm to room temperature.

At the end of the reaction the mixture is decomposed by admixing it with a base, such as aqueous potassium hydrocarbonate solution. The product is extracted with a water-immiscible organic solvent, the solution is washed until neutral, dried, and the solvent is evaporated to obtain a 3-chloro-pregnane derivative of the formula (I) wherein X is acetyl or chloroacetyl group.

If desired, the resulting product can be subjected to acidic or alkaline hydrolysis to obtain the respective compound of the formula (I) wherein X is hydrogen. Hydrolysis is performed preferably in a solvent which is at least partially miscible with water, such as in an alcohol or in a mixture of a solvent for the steroid (e.g. benzene) and an alcohol, at a temperature between room temperature and the boiling point of the reaction mixture. Alkaline hydrolysis is performed preferably with an alkali metal carbonate or hydrocarbonate, whereas acid hydrolysis is performed preferably with a mineral acid, such as hydrochloric acid, sulfuric acid or perchloric acid, or an organic acid, such as formic acid, acetic acid or trifluoroacetic acid.

When a compound of the formula (I) wherein X is hydrogen is to be prepared, the X' acyl group of the starting substance of the formula (II) is selected preferably so that its hydrolytic splitting can be performed under optimum conditions which do not damage substituents Y and Z already present in the molecule. Thus when a compound of the formula (I) wherein X is hydrogen and Y and Z stand for fluorine is to be prepared, it is preferred to use a compound of the formula (II) wherein Y and Z stand for fluorine and X' is monochloroacetyl group as starting substance, and to perform the hydrolysis under mild alkaline conditions. In this latter step the 3-chloro-21-monochloroacetoxy derivative can be dissolved e.g. in a mixture of benzene and methanol, and an aqueous solution of an alkali metal carbonate or hydrocarbonate can be utilized as hydrolysing agent. On the other hand, when a 21-hydroxysteroid of the formula (I) wherein Y is bromine and Z is fluorine is to be prepared, it is preferred to start from the respective compound of the formula (II) wherein X' is acetyl, and to hydrolyze the resulting 3-chloro-21-acetoxy-steroid with an aqueous acid is methanol solution or suspension.

The reaction mixture obtained after hydrolysis can be processed in a manner known per se, e.g. by extracting the product with a water-immiscible organic solvent, washing the extract to neutral, drying, and evaporating the solvent.

The 3-chloro-pregnane derivatives according to the invention possess valuable glucocorticoidal effects. In the comparative tests described below these effects of 9α-fluoro-3-chloro-11β,16α,17β,21-tetrahydroxy-pregna-1,3,5-triene-20-one-16,17-acetonide (3-chloro-TCA), 6,9α-difluoro-3-chloro-11β,16α,17α,21-tetrahydroxypregna-1,3,5-triene-20-one-16,17-acetonide (3-chloro-FCA) and 6-bromo-9α-fluoro-3-chloro-11β,16α,17α,21-tetrahydroxy-pregna-1,3,5-triene-20-one-16,17-acetonide (3-chloro-6-bromo-TCA) were examined, and 9α-fluoro-11β,16α,17α,21-tetrahydroxy-pregna-1,4-diene-3,20-dione-16,17-acetonide (TCA) and 6α,9α-difluoro-11β,16α,17α,21-tetrahydro-pregna-1,4-diene-3,20-dione-16,17-acetonide (FCA), two known compounds with glucocorticoidal effects, were utilized as comparative substances.

The affinity of the above compounds to rat liver glucocorticoid receptors, which is a precondition of glucocorticoidal effect, was tested according to the method of Baxter et al. [J. D. Baxter, G. M. Tomkins: "Specific Cytoplasmic Glucocorticoid Receptors in Hepatome Tissue Culture Cells", Proc. Natl. Acad. Sci. USA 68, 932–937 (1971)]. On the basis of literature data the apparent dissociation constant of TCA is 10 nM [see. A. Munck and K. Leung: "Receptors and Mechanism of Action of Steroid Hormones", Ed. J. R. Pasqualini; Marcell Dekker, New York, 1977, p. 343]. The apparent dissociation constant of 3-chloro-TCA is 30 nM, that of fluocinolon-acetonide is 15 nM and that of 3-chloro-FCA is 25 nM, i.e. the dissociation constants of these three compounds are of the same order. On the other hand, the apperent dissociation constant of 3-chloro-6-bromo-TCA is 60 nM.

In order to confirm the results of the above tests, the effects of TCA and 3-chloro-TCA on tyrosine aminotransferase induction were also tested in chickens and rats [T. I. Diamandstone: "Assay of Tyrosine Transaminase Activity by Conversion of p-Hydroxyphenylpyruvate to p-Hydroxybenzaldehyde", Anal. Biochem. 16, 395–401 (1966)]. In these tests TCA exerted 50% inductive effect in concentrations of 0.15 μg/mg and 0.025 μg/mg, respectively, whereas 3-chloro-TCA showed the same effect in concentrations of 0.05 mg/100 g and 0.005 mg/100 g, respectively.

It is known that glucocorticoids cause thymus involution [O. Greengard, R. Machovich: "Hydrocortisone Regulation of Thymidine Kinase in Thymus Involution and Hematopoietic Tissues", Biochem. Biophys. Acta 286, 382–388 (1972)]. 50% reduction of thymus weight was observed on chickens with a dose of 0.01 mg/100 g and on rats with a dose of 0.001 mg/100 g for both TCA and 3-chloro-TCA.

The results of other pharmacological tests are summarized in the following tables.

Systemic antiphlogistic effect (a) Inhibition of carrageenin-induced planter oedema [Winter et al.: J. Pharm. Exp. Therap. 369 (1963)]

| Substance | Doses mg/kg p.o. | Inhibition % |
|---|---|---|
| 3-Chloro-TCA-21-acetate | 2 | 8.9 |
|  | 6 | 9.6 |
| 3-Chloro-TCA | 2 | 30.2 |
|  | 6 | 38.7 |

(b) Granuloma pouch test according to Selye [J. Selye: Recent Progr. Horm. Res. 8, 117 (1953)]

| Substance | Doses mg/kg s.c. | Inhibition % |
|---|---|---|
| 3-Chloro-TCA-21-acetate | 0.5 | 56.6 |
|  | 1.5 | 73.3 |
| 3-Chloro-TCA | 0.5 | 90.8 |
|  | 1.5 | 90.1 |

(c) Cotton granuloma test [C. A. Winter et al: J. Pharm. Exp. Therap. 141, 369 (1963)]

| Substance | Doses mg/kg s.c. | Inhibition % |
|---|---|---|
| 3-Chloro-TCA-21-acetate | 0.5 | 33.0 |
|  | 1.5 | 91.0 |
| 3-Chloro-TCA | 0.5 | 22.0 |
|  | 1.5 | 26.0 |

Local antiphlogistic effect (a) Local pouch test according to Selye [Bianchetti et al.: Arzneim. Forsch. 27, 2096 (1977)]

| Substance | Doses mg/pouch | Inhibition % |
|---|---|---|
| 3-Chloro-TCA-21-acetate | 0.033 | 12.4 |
|  | 0.10 | 26.3 |
| 3-Chloro-TCA | 0.033 | 26.0 |
|  | 0.10 | 32.3 |

(b) Local cotton granuloma test [B. Silvestrini: Arzneim. Forsch. 19, 30 (1969)]

| Substance | Doses mg/cotton | Inhibition % |
|---|---|---|
| 3-Chloro-TCA-21-acetate | 0.033 | 52.4 |
|  | 0.10 | 35.3 |
| 3-Chloro-TCA | 0.033 | 24.1 |
|  | 0.10 | 51.4 |

(c) Inhibition of ear inflammation provoked by croton oil [Tonelli et al.: Endocrinology 77, 625 (1965)]

| Substance | Doses mg/ml | Inhibition % |
|---|---|---|
| 3-Chloro-TCA-21-acetate | 0.02 | 10.0 |
|  | 0.10 | 17.8 |
| 3-Chloro-TCA | 0.02 | 30.0 |
|  | 0.10 | 52.9 |

The new compounds of the formula (I) can be converted into pharmaceutical compositions, such as tablets, capsules, pills, injectable solutions or suspensions, ointments, etc., according to known techniques, by utilizing conventional pharmaceutical additives (such as carriers, fillers, disintegrating aids, lubricants, coloring agents, flavoring agents, etc.).

The invention is elucidated in detail by the aid of the following non-limiting examples.

EXAMPLE 1

Preparation of 3-chloro-9α-fluoro-11β,16α,17α,21-tetrahydroxy-pregna-1,3,5-triene-20-one-16,17-acetonide-21-acetate 14 ml (152.0 mmoles) of phosphorous oxychloride are added dropwise to a stirred mixture of 120 ml of dichloromethane and 45 ml of dimethyl formamide at −10° C., and the mixture is maintained at −10° C. for 20 minutes. Thereafter a suspension of 23.8 g (49.95 mmoles) of 9α-fluoro-11β,16α,17α,21-tetrahydroxy-pregna-1,4-diene-3,20-dione-16,17-acetonide-21-acetate in a mixture of 0.5 ml of pyridine and 200 ml of dichloromethane is added to the mixture at a temperature below 0° C. The mixture is stirred for 20 minutes, then diluted with 200 ml of dichloromethane, and the solution is poured into an ice-cold solution of 60.9 g potassium hydrocarbonate in 1200 ml of water. The mixture is stirred for 30 minutes, thereafter the phases are separated, and the aqueous phase is extracted twice with 200 ml of dichloromethane, each. The organic phases are combined, washed with water, dried over anhydrous sodium sulfate, and then evaporated. The residual crude product is dissolved in 200 ml of acetone, and the solution is dropped into 2 liters of ice-cold aqueous 10% sodium chloride solution. The mixture is stirred, the separated product is filtered off, washed with water, and then dried at room temperature in vacuo over phosphorous pentoxide under protecting it from light. 24.2 g (97.8%) of 3-chloro-9α-fluoro-11β,16α,17α,21-tetrahyroxy-pregna-1,3,5-triene-20-one-16,17-acetonide-21-acetate are obtained; the yellow substance melts at 187°–190° C. under decomposition. After recrystallization from acetone and methanol the product starts to melt at 215° C. and decomposes at 222°–228° C.

Analysis: Cl: found: 6.65%, 6.83% (calculated: 7.16%).

IR spectrum: 3460 ($\nu$ —OH), 1755 ($\nu$ >C=O, acetate), 1730 ($\nu$ >C=O, $C_{20}$ carbonyl), 1615 ($\nu$ >C=C<), 1055 ($\nu$ C—O, acetonide) $cm^{-1}$.

EXAMPLE 2

Preparation of 3-chloro-9α-fluoro-11β,16α,17α,21-tetrahydroxy-pregna-1,3,5-triene-20-one-16,17-acetonide 7.42 g (14.99 mmoles) of 3-chloro-9α-fluoro-11β,16α,17α,21-tetrahydroxy-pregna-1,3,5-triene-20-one-16,17-acetonide-21-acetate are dissolved in a mixture of 750 ml of methanol and 300 ml of benzene under stirring and introducing nitrogen gas into the mixture. The solution is stirred at room temperature for 15 minutes and then a solution of 3.0 g (29.96 mmoles) of potassium hydrocarbonate in 22.5 ml of distilled water is added. Stirring is continued at room temperature for 3 hours, then the slightly alkaline (pH: 7.5) solution is acidified to pH 6.5 with acetic acid. The solvent is evaporated under reduced pressure at a temperature below 40° C., and 100 ml of ice-cold water are added to the residue. The solid product is separated, washed with ice-cold water, and dried at room temperature in vacuo over phosphorous pentoxide under protecting it from light. The resulting 6.75 g of crystalline crude product are recrystallized from 650 ml of ether. 5 g (73.6%) of 3-chloro-9α-fluoro-11β,16α,17α,21-tetrahydroxy-pregna-1,3,5-triene-20-one-16,17-acetonide are obtained; m.p.: 229°–231° C.

Analysis: Cl: found: 7.52%, 7.97% (calculated: 7.83%).

IR spectrum: 3580, 3450 (ν —OH), 1715 (ν >C=O, $C_{20}$ carbonyl), 1618 (ν C=C), 1055 (ν C—O, acetonide), 1382, 1373 ($δ_s$ —$CH_3$, geminal methyl groups of the acetonide) $cm^{-1}$.

EXAMPLE 3

Preparation of
3-chloro-9α-fluoro-11β,16α,17α,21-tetrahydroxy-pregna-1,3,5-triene-20-one-16,17-acetonide-21-monochloroacetate 6.72 ml (72.8 mmoles) of phosphorous oxychloride are added dropwise to a mixture of 120 ml of dichloromethane and 21.6 ml of dimethyl formamide at 0° C. The mixture is stirred at 0° C. for 20 minutes, then cooled to −10° C., and a solution of 11.8 g (23.14 mmoles) of 9α-fluoro-11β,16α,17α,21-tetrahydroxy-pregna-1,4-diene-3,20-dione-16,17-acetonide-21-monochloroacetate in a mixture of 0.24 ml of pyridine and 120 ml of dichloromethane is added dropwise at this temperature. The mixture is maintained at −5° C. for 50 minutes, and then poured into a solution of 29.16 g of sodium hydrocarbonate in 800 ml of water. After 30 minutes of stirring the separated precipitate is filtered off, washed with water, and dried in vacuo at room temperature. 8.45 g (66.5%) of 3-chloro-9α-fluoro-11β,16α,17α,21-tetrahydroxy-pregna-1,3,5-triene-20-one-16,17-acetonide-21-monochloroacetate are obtained; m.p.: 266°–268° C.

Analysis: Cl: found: 12.89% (calculated: 13.39%).

IR spectrum: 3450 (ν —OH), 1771 (ν >C=O, chloroacetate), 1729 (ν >C=O, $C_{20}$ carbonyl), 1612 (ν C=C), 1378, 1360 ($δ_s$, —$CH_3$, geminal methyl groups in the acetonide), 1053 (ν —C—O—, acetonide) $cm^{-1}$.

EXAMPLE 4

Preparation of
3-chloro-9α-fluoro-11β,16α,17α,21-tetrahydroxy-pregna-1,3,5-triene-20-one-16,17-acetonide 6.35 g (11.99 mmoles) of 3-chloro-9α-fluoro-11β,16α,17α,21-tetrahydroxy-pregna-1,3,5-triene-20-one-16,17-acetonide-21-monochloroacetate are suspended in a mixture of 600 ml of methanol and 240 ml of benzene at room temperature under stirring and bubbling nitrogen gas through the mixture. The suspension is stirred for 20 minutes, and then a solution of 2.4 g (23.97 mmoles) of potassium hydrocarbonate in 18 ml of boiled and demineralized water is added. The steroid dissolves gradually, but the reaction mixture remains hazy even after 2 hours. Then the pH of the mixture is adjusted to 6–6.5 with acetic acid, and the solvent is evaporated under reduced pressure at a temperature below 40° C. The solid residue is admixed with water, filtered off, washed with water and dried. The resulting 5.4 g of crude product are recrystallized from ether. 4.05 g (75%) of 3-chloro-9α-fluoro-11β,16α,17α,21-tetrahydroxy-pregna-1,3,5-triene-20-one-16,17-acetonide are obtained; m.p.: 221°–222° C.

Analysis: Cl: found: 7.64% (calculated: 7.83%).

IR spectrum: the same as given in Example 2.

EXAMPLE 5

Preparation of
3-chloro-6,9α-difluoro-11β,16α,17α,21-tetrahydroxy-pregna-1,3,5-triene-20-one-16,17-acetonide-21-monochloroacetate 0.48 ml (5.2 mmoles) of phosphorous oxychloride is added dropwise to a mixture of 10 ml of dichloromethane and 1.53 ml of dimethyl formamide at −10° C. The solution is stirred at −10° C. for 20 minutes, and then a solution of 0.9 g (1.7 mmoles) of 6α,9α-difluoro-11β,16α,17α,21-tetrahydroxy-pregna-1,4-diene-3,20-dione-16,17-acetonide-21-monochloroacetate in a mixture of 0.02 ml of pyridine and 20 ml of dichloromethane is added. The mixture is allowed to warm to room temperature, stirred at 25°–26° C. for 5 hours, then diluted with 30 ml of dichloromethane and dropped into a solution of 2.08 g (20.8 mmoles) of potassium hydrocarbonate in 100 ml of water. After 20 minutes of stirring the phases are separated, the aqueous phase is extracted three times with 30 ml of dichloromethane, each, the organic phases are combined, washed twice with 50 ml of water, each, dried over anhydrous sodium sulfate and filtered. The solvent is evaporated under reduced pressure at 30° C., the solid residue is triturated with ether, filtered off, and dried at room temperature in vacuo under protecting it from light. 0.69 g (74%) of 3-chloro-6,9α-difluoro-11β,16α,17α,21-tetrahydroxy-pregna-1,3,5-triene-20-one-16,17-acetonide-21-monochloroacetate is obtained; m.p.: 238°–243° C.

Analysis: Cl: found: 13.40%, 13.47% (calculated: 12.95%).

EXAMPLE 6

Preparation of
3-chloro-6,9α-difluoro-11β,16α,17α,21-tetrahydroxy-pregna-1,3,5-triene-20-one-16,17-acetonide 0.55 g (1.0 mmole) of 3-chloro-6,9α-difluoro-11β,16α,17α,21-tetrahyroxy-pregna-1,3,5-triene-20-one-16,17-acetonide-21-monochloroacetate is dissolved under stirring in a mixture of 30 ml of benzene and 80 ml of methanol, the solution is stirred at room temperature under nitrogen atmosphere for 15 minutes, and then a solution of 0.2 g (2.0 mmoles) of potassium hydrocarbonate in 1.5 ml of boiled, demineralized water is added. The reaction mixture turns hazy, and then gets clear again within 15 minutes. The pH of the mixture is 7.5–8. The mixture is stirred at 28° C. for 35 minutes, then acidified to pH ~6 with acetic acid, and the solvent is evaporated under reduced pressure at a temperature below 40° C. The solid residue is triturated with water, filtered off, washed with water, and dried in vacuo under protecting it from light. The resulting 0.41 g of crystalline crude product is recrystallized from ether. 0.37 g (78.7%) of 3-chloro-6,9α-difluoro-11β,16α,17α,21-tetrahydroxy-pregna-1,3,5-triene-20-one-16,17-acetonide is obtained; m.p.: 225°–229° C.

IR spectrum: 3510, 3420 (ν —OH), 1720 (ν >C=O, $C_{20}$ carbonyl), 1678, 1623 (ν C=C), 1052 (ν C—O, acetonide) $cm^{-1}$.

EXAMPLE 7

Preparation of 3-chloro-6-bromo-9α-fluoro-11β,16α,17α,21-tetrahydroxy-pregna-1,3,5-triene-20-one-16,17-acetonide 1.12 ml (12.2 mmoles) of phosphorous oxychloride are added dropwise to a mixture of 10 ml of dichloromethane and 3.6 ml of dimethyl formamide at 0° C. The mixture is stirred at 0° C. for 20 minutes, then cooled to −8° C., and a solution of 2.22 g (4.0 mmoles) of 6-bromo-9α-fluoro-11β,16α,17α,21-tetrahydroxy-pregna-1,4-diene-3,20-dione-16,17-acetonide-21-acetate in a mixture of 0.04 ml of pyridine and 20 ml of dichloromethane is added dropwise. The mixture is stirred at a temperature between −10° C. and 0° C. for one hour and then at room temperature for 4.5 hours. Thereafter the mixture is allowed to stand at 2°-5° C. for 15 hours in order to attain complete reaction. The mixture is diluted with 20 ml of dichloromethane, 20 ml of a 20% aqueous sodium acetate solution are added, the mixture is stirred at room temperature for 30 minutes, and then the phases are separated. The aqueous phase is extracted twice with 20 ml of dichloromethane, each, the organic phases are combined, washed with aqueous sodium bicarbonate solution and water, dried over anhydrous sodium sulfate, and the solvent is evaporated under reduced pressure. The resulting 2.95 g of crude oily product are dissolved in 30 ml of acetone, and the solution is dropped into water. The separated product is filtered off and dried. 2.0 g (87.3%) of 3-chloro-6-bromo-9α-fluoro-11β,16α,17α,21-tetrahydroxy-pregna-1,3,5-triene-20-one-16,17-acetonide-21-acetate are obtained as a pale yellow, crystalline substance. 1.14 g of this product are suspended in 40 ml of methanol, and 10.0 ml of a 67% aqueous perchloric acid solution are added dropwise to the stirred solution at room temperature. The resulting suspension is stirred for one hour and then 10 ml of dichloromethane are added to it. The resulting homogeneous solution is stirred for 8 hours and then dropped into 100 ml of a 1% aqueous sodium bicarbonate solution. The resulting mixture is extracted three times with 50 ml of dichloromethane, each. The dichloromethane solutions are combined, washed with 1% aqueous sodium bicarbonate solution and then with water until neutral, dried over anhydrous sodium sulfate, and the solvent is evaporated under reduced pressure. The crude, crystalline residue is treated with a 1:5 mixture of ether and petroleum ether, the solid is filtered off and dried in vacuo. 1.0 g (94.3%) of 3-chloro-6-bromo-9α-fluoro-11β,16α,17α,21-tetrahydroxy-pregna-1,3,5-triene-20-one-16,17-acetonide is obtained. The product melts at 191°-194° C. after recrystallization from ether.

IR spectrum: 3500 ($\nu$ C$_{21}$—OH), 3440 ($\nu$ C$_{11}$—OH), 1715 ($\nu$ >C=O, C$_{20}$ carbonyl), 1638, 1602, 1562 ($\nu$ C=C), 1382, 1375 ($\delta_s$ —CH$_3$, geminal methyl groups in the acetonide), 1055 ($\nu$ C—O—, acetonide) cm$^{-1}$.

What we claim is:

1. A process for the preparation of a $\Delta^{1,3,5}$-3-chloro-pregnane derivative of formula (I)

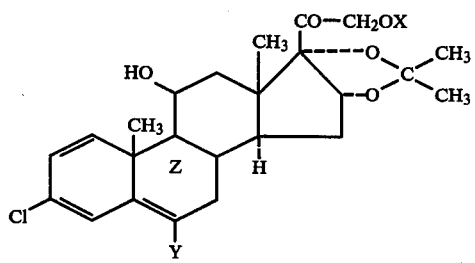

wherein
X is hydrogen, acetyl or chloroacetyl, and
Y is hydrogen or halogen, and Z is halogen, characterized in that a $\Delta^{1,4}$-3-oxo-pregnane derivative of the formula (II),

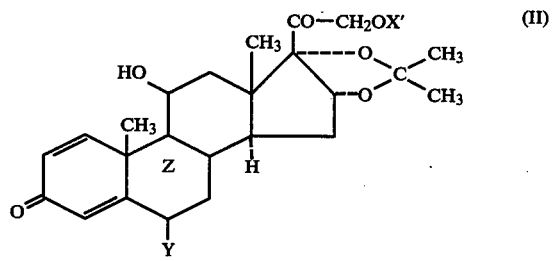

wherein X' is acetyl or chloroacetyl, is reacted with a chloromethyleneiminium salt of the formula (III)

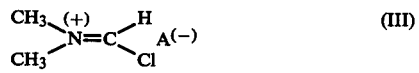

wherein A$^{(-)}$ represents a salt-forming anion in an aprotic solvent in the presence of a tertiary base, and a resulting compound of the formula (I) wherein X is acetyl or a chloroacetyl can be subjected to hydrolysis to obtain a compound of the formula (I) wherein X is hydrogen.

2. A process as claimed in claim 1, characterized in that a lower halogenated hydrocarbon and/or dimethyl formamide is applied as aprotic solvent.

3. A process as claimed in claim 1, characterized in that pyridine or an alkylated derivative thereof is used as tertiary base.

4. A process for the preparation of a pharmaceutical composition, characterized in that a compound of the formula (I), wherein X, Y and Z are as defined in claim 1, is admixed with a pharmaceutically acceptable carrier, diluent or additive.

5. A $\Delta^{1,3,5}$-3-chloro-pregnane derivative of the formula (I)

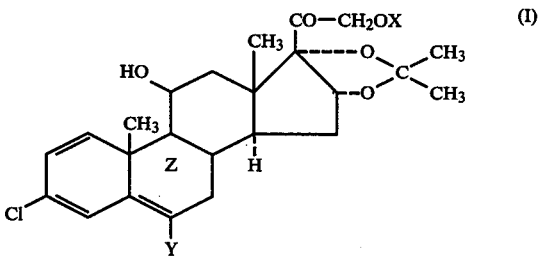

wherein
X is hydrogen, acetyl or chloroacetyl,
Y is hydrogen or halogen, and Z is halogen.

6. A pharmaceutical composition comprising an effective amount of a compound of the formula (I) as defined in claim 5, together with a pharmaceutically acceptable carrier, diluent or additive.

7. An antiphlogistic method of treatment which comprises administering an effective amount of a compound as defined in claim 5 to an afflicted subject to ameliorate a condition responsive to antophlogisics.

* * * * *